United States Patent
Becker et al.

(10) Patent No.: US 11,759,641 B2
(45) Date of Patent: Sep. 19, 2023

(54) IMPLANTABLE MEDICAL DEVICE FOR STIMULATING THE HIS BUNDLE OF A HUMAN OR ANIMAL HEART EMPLOYING AN ADAPTED IMPEDANCE MEASUREMENT

(71) Applicant: BIOTRONIK SE & Co. KG, Berlin (DE)

(72) Inventors: Frank Becker, Berlin (DE); Stefan Paule, Drosendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/768,721

(22) PCT Filed: Oct. 22, 2020

(86) PCT No.: PCT/EP2020/079735
§ 371 (c)(1),
(2) Date: Apr. 13, 2022

(87) PCT Pub. No.: WO2021/078848
PCT Pub. Date: Apr. 29, 2021

(65) Prior Publication Data
US 2022/0355117 A1    Nov. 10, 2022

(30) Foreign Application Priority Data
Oct. 24, 2019  (EP) .................................... 19205046

(51) Int. Cl.
*A61N 1/365* (2006.01)
*A61N 1/05* (2006.01)
(Continued)

(52) U.S. Cl.
CPC ........ *A61N 1/36521* (2013.01); *A61B 5/0538* (2013.01); *A61N 1/056* (2013.01);
(Continued)

(58) Field of Classification Search
CPC . A61N 1/36521; A61N 1/36585; A61N 1/056
See application file for complete search history.

(56) References Cited

U.S. PATENT DOCUMENTS

| | | | |
|---|---|---|---|
| 2012/0239106 A1* | 9/2012 | Maskara | A61N 1/371 607/28 |
| 2014/0107724 A1 | 4/2014 | Shuros et al. | |
| 2019/0111265 A1 | 4/2019 | Zhou | |

FOREIGN PATENT DOCUMENTS

EP     1234597 A2    8/2002

OTHER PUBLICATIONS

International Search Report (PCT/ISA/210) and Written Opinion (PCT/ISA/237) dated Feb. 17, 2021, by the European Patent Office as the International Searching Authority for International Application No. PCT/EP2020/079735.

* cited by examiner

*Primary Examiner* — Alyssa M Alter
(74) *Attorney, Agent, or Firm* — Buchanan Ingersoll & Rooney PC

(57) ABSTRACT

An implantable medical device for stimulating a human/animal heart, comprising a housing, a processor, a memory unit, a stimulation unit configured to stimulate the His bundle, and a detection unit configured to detect an electrical signal at the His bundle. The device performs: a) stimulating the His bundle with a stimulation pulse delivered by the stimulation unit; b) measuring an electric signal at the His bundle with the detection unit upon termination of a first period of time starting upon delivering of the stimulation pulse, wherein the first period of time is from 35 ms to 500 ms; c) measuring an impedance of the same heart with the detection unit upon termination of a second period of time starting upon delivering of the stimulation pulse, wherein (Continued)

the second period of time is equal to or longer than the first period of time and is from 50 ms to 500 ms.

15 Claims, 3 Drawing Sheets

(51) Int. Cl.
    *A61N 1/372*     (2006.01)
    *A61N 1/368*     (2006.01)
    *A61N 1/375*     (2006.01)
    *A61B 5/0538*     (2021.01)

(52) U.S. Cl.
    CPC ............. *A61N 1/365* (2013.01); *A61N 1/368* (2013.01); *A61N 1/3684* (2013.01); *A61N 1/36585* (2013.01); *A61N 1/3752* (2013.01); *A61N 1/37223* (2013.01); *A61N 1/37235* (2013.01); *A61N 1/37247* (2013.01); *A61N 1/37252* (2013.01)

IMPLANTABLE MEDICAL DEVICE FOR STIMULATING THE HIS BUNDLE OF A HUMAN OR ANIMAL HEART EMPLOYING AN ADAPTED IMPEDANCE MEASUREMENT

CROSS-REFERENCE TO RELATED APPLICATIONS

This application is the United States National Phase under 35 U.S.C. § 371 of PCT International Patent Application No. PCT/EP2020/079735, filed on Oct. 22, 2020, which claims the benefit of European Patent Application No. 19205046.6, filed on Oct. 24, 2019, the disclosures of which are hereby incorporated by reference herein in their entireties.

TECHNICAL FIELD

The present invention relates to an implantable medical device for stimulating a human or animal heart according to the preamble of claim 1, to a method for controlling the operation of such an implantable medical device according to the preamble of claim 13, and to a computer program product according to the preamble of claim 14.

BACKGROUND

Implantable medical devices for stimulating a human or animal heart, such as pacemakers, have been known for a long time. They can perform different functions. Different stimulation programs can be carried out by an appropriate pacemaker to restore the treated heart to a normal state. Pacemakers are also known to stimulate the His bundle.

The His bundle is a bundle of specific heart muscle cells that is part of the cardiac conduction system. The His bundle is located distally of the atrioventricular node towards the apex of the heart.

There exist specific devices adapted for His bundle pacing, wherein a detecting (sensing) and stimulation electrode is not implanted into the ventricle of the human or animal heart to be treated, but rather at or near to the His bundle of the heart. Such use of a His bundle electrode enables a particularly physiologic stimulation of the human or animal heart. However, the usual way to measure the impedance between an electrode implanted into an apical region of the right ventricle and a housing of the implantable medical device is no longer available in such a case. Nonetheless, the impedance is an important measure of the contractility of the treated heart so that it is also desired to measure the impedance with devices specifically adapted for His bundle pacing. In such devices, the impedance needs to be measured with the His bundle electrode. However, this cannot be done with the parameters used for conventional implantable medical devices measuring electric cardiac signals in the right ventricle of a stimulated heart.

The present disclosure is directed toward overcoming one or more of the above-mentioned problems, though not necessarily limited to embodiments that do.

SUMMARY

It is an object of the present invention to provide an implantable medical device for stimulating the His bundle of a human or animal heart that enables reliable impedance measurements of the heart.

At least this object is achieved with an implantable medical device for stimulating a human or animal heart having the features of claim 1. Such an implantable medical device comprises a housing, a processor, a memory unit, a stimulation unit and a detection unit. The stimulation unit is configured to stimulate the His bundle of a human or animal heart. The detection unit is configured to detect an electrical signal at the His bundle of the same heart. In this context, the detection unit comprises an electrode having at least a first electrode pole.

According to an aspect of the presently claimed invention, the memory unit comprises a computer-readable program that causes the processor to perform the steps explained in the following when executed on the processor.

First, the His bundle of a human or animal heart is stimulated with a stimulation pulse delivered by the stimulation unit.

Upon delivering of the stimulation pulse, a first period of time starts. When the first period of time is terminated (i.e., directly at the end of the first period of time), an electric signal at the His bundle of the same heart is measured with the detection unit. In this context, the first period of time lies in time range of from 35 ms to 500 ms.

Upon delivering of the stimulation pulse, also a second period of time starts. When this second period of time is terminated (i.e., directly at the end of the second period of time), an impedance of the same heart is measured with the detection unit. The second period of time is equal to or longer than the first period of time. Additionally, it lies in a time range of from 50 ms to 500 ms.

Thus, the impedance measurement starts at the earliest directly at the end of the first period of time (if the second period of time is as long as the first period of time). Then, the first period of time defines the delay between the stimulation pulse and the start of the impedance measurement. This embodiment is in particular appropriate if the first period of time lies in a time range of from 50 ms to 500 ms, in particular from 100 ms to 400 ms, in particular from 200 ms to 300 ms, in particular from 250 ms to 300 ms, in particular from 260 ms to 285 ms, in particular from 270 ms to 280 ms.

If the second period of time is longer than the first period of time, the time delay between the stimulation pulse at the start of the impedance measurement is defined by the second period of time. Then, it is possible to already obtain detailed information on the electrical signal at the His bundle after the first period of time is terminated but the second period of time is still running so that the impedance measurement has not yet been started. Thus, it is possible to record an intracardiac electrogram (IEGM) prior to starting the impedance measurement in order to obtain detailed information on the cardiac rhythm before and at the start of the impedance measurement.

The ingenious arrangement of the delay intervals (i.e., the first period of time and the second period of time) makes it possible to take into account a time between a stimulation of the His bundle and the transition of the electrical stimulus through the His-Purkinje system to the right ventricle of the stimulated heart in order to finally result in a depolarization and thus contraction of the heart.

While typical impedance measurements performed with a right ventricular electrode start immediately after stimulating the right ventricle or after a very short blanking period, such an approach would not be feasible with the His bundle electrode due to the physiologic delay of contraction of the heart in response to a stimulus at the His bundle. The presently claimed invention provides, in an aspect, an easily applicable solution so as to be able to also measure a cardiac impedance with a His bundle electrode.

The first period of time can also be denoted as a blanking period. During this blanking period, the sensing unit will not detect an electrical signal at the His bundle. Thus, it will not be possible to record an IEGM during this period of time. Furthermore, it will not be possible during the first period of time to measure an impedance based on electric signals delivered to the His bundle of the stimulated heart.

In an embodiment, the first period of time is chosen such that it extends over an R wave, i.e., over a cardiac response to the stimulation pulse delivered to the His bundle of the heart. It is important to measure the impedance only at the end of such an R wave in order to not detect changes of impedance during the R wave, but rather at a final section of the R wave or after the R wave has been terminated. Only then, the impedance signal will deliver reliable information on the contractility of the stimulated heart.

If the second period of time equals the first period of time, the blanking window extends over the R wave without concrete knowledge if the R wave is really terminated at the start of the impedance measurement. While this approach is particularly simple and requires less computational effort (and thus less energy consumption), it is sometimes desirable to obtain more detailed knowledge on the specific cardiac cycle prior to and at the beginning of the impedance measurement.

To address this need, the second period of time can be longer than the first period of time. Then, electric signals can be obtained at the His bundle of the stimulated heart to produce an IEGM prior to the impedance measurement. Consequently, concrete information on the cardiac cycle due to recording of an IEGM is obtained. The impedance measurement only starts during a final section or after termination of the R wave. Since in this variant IEGM information on the cardiac cycle is available in addition to the impedance signals, a direct mapping of the impedance signals to the IEGM signals can be made. Then, it is particularly simple to see if the impedance measurement really relates to a time frame starting during a final section or after the termination of the R wave directly after the stimulation pulse, as intended. Thus, this variant provides a user with more information on the cardiac cycle, though it requires somewhat more energy to record an IEGM over an extended period of time.

In an embodiment, the first period of time is shorter than the second period of time and lies in a time range of from 35 ms to 110 ms, in particular from 45 ms to 100 ms, in particular from 55 ms to 90 ms, in particular from 60 ms to 80 ms, in particular from 65 ms to 75 ms.

In an embodiment, the second period of time lies in a time range of from 50 ms to 500 ms, in particular from 100 ms to 400 ms, in particular from 200 ms to 300 ms, in particular from 250 ms to 300 ms, in particular from 260 ms to 285 ms, in particular from 270 ms to 280 ms.

In an embodiment, the implantable medical device is an implantable pulse generator (IPG), an implantable cardioverter-defibrillator (ICD), or a device for cardiac resynchronization therapy (CRT).

In an embodiment, the computer-readable program causes the processor to determine and set a sensing threshold prior to the start of measuring an electric signal at the His bundle. In this context, the sensing threshold is lower than a signal of an R wave so that an R wave is reliably detected even if the sensing threshold is determined and set. At the same time, the sensing threshold is higher than a signal of the P wave of the cardiac contraction and higher than the His bundle signal. Thus, the P wave and His bundle signal will not be detected after having set the sensing threshold. This significantly reduces the electric signals detected by the sensing unit so that the energy consumption for the sensing is significantly reduced. Still then, the relevant information on the R wave of a cardiac contraction following the stimulation of the His bundle can be reliably detected so as to have concrete knowledge whether the impedance measurement starts only after or during a final section of the R wave.

In an embodiment, the computer-readable program causes the processor to perform the step of measuring the impedance without having detected an R wave of a cardiac contraction between the step of stimulating the His bundle and the step of measuring an impedance, wherein this cardiac contraction has been evoked by the stimulation pulse. Thus, this embodiment relates to a non-knowledge of the correct occurrence of an R wave upon stimulating the His bundle. As explained above, this embodiment can be particularly easy carried out by setting the second period of time to be as long as the first period of time. This embodiment does not provide detailed information on the cardiac cycle at the beginning of the impedance measurement but requires less energy than other embodiments.

In an embodiment, the computer-readable program causes the processor to detect an R wave of the cardiac contraction prior to the step of measuring the impedance. In this context, the cardiac contraction is once again being evoked by the stimulation pulse. Thus, this embodiment relates to an operational mode of the implantable medical device that provides more detailed information on the cardiac cycle of the stimulated heart but requires more energy to sense the electrical signals at the His bundle than in case of the precedingly explained variant that employs a longer blanking period (i.e., a longer first period of time and an equally long second period of time).

In an embodiment, the computer-readable program causes the processor to terminate the second period of time after having detected an R wave upon decreasing signal intensities of the R wave. Thus, this embodiment employs an automatic adaptation of the length of the second period of time in dependence on the R wave evoked by the previous stimulation pulse.

In an embodiment, the second period of time comprises a first sub-period, second sub-period, and a third sub-period. In this context, the first sub-period corresponds to the first period of time. Furthermore, the second sub-period extends from an end of the first sub-period until a detection of a right ventricular event. Thus, the second sub-period is a variable period, the length of which is determined by the time needed to detect an R wave after the end of the first period of time. The third sub-period starts at the end of the second sub-period without gap between the second sub-period and the third sub-period. In an embodiment the first sub-period lies in a time range of from 35 ms to 110 ms, in particular from 45 ms to 100 ms, in particular from 55 ms to 90 ms, in particular from 60 ms to 80 ms, in particular from 65 ms to 75 ms. The third sub-period is invariant. The second sub-period lies in a time range of from 10 ms to 50 ms. The third sub-period lies in a time range of from 10 ms to 100 ms, in particular from 20 ms to 80 ms, in particular from 30 ms to 70 ms, in particular from 40 ms to 60 ms, in particular from 45 ms to 55 ms.

In an embodiment, the computer-readable program causes the processor to conduct a plurality of impedance measurements during a third period of time. In this context, the third period of time starts directly at the end of the second period of time. The third period of time lies in a time range of from 50 ms to 400 ms, in particular from 100 ms to 350 ms, in particular from 200 ms to 320 ms, in particular from 220 ms to 300 ms, in particular from 240 ms to 260 ms.

In an embodiment, the third period of time, i.e., the impedance measuring time, is longer than the impedance measuring time of conventional pacemakers performing an impedance measurement with a right ventricular electrode. Then, the impedance can be safely determined even if a change in impedance extends over a longer period of time than in case of a right ventricular stimulation of the heart and/or a right ventricular impedance measurement. In this embodiment, the third period of time lies in a time range of from 250 ms to 400 ms, in particular from 270 ms to 350 ms.

In an embodiment, the computer-readable program causes the processor to automatically adapt an initial value of an amplitude of current pulses used for measuring the impedance. In this context, the amplitude values can be chosen from an amplitude range of from 5 µA to 1000 µA, in particular from 10 µA to 900 µA, in particular from 20 µA to 800 µA, in particular from 40 µA to 600 µA, in particular from 50 µA to 600 µA. By such an adaptation of the amplitude of current pulses, variations of the concrete implantation site of the His bundle electrode can be compensated. If the His bundle has been exactly hit upon implantation of the His bundle electrode, lower amplitudes of the current pulses used for measuring the impedance will be sufficient to obtain reliable measuring values. If, however, the His bundle electrode does not exactly match the His bundle, higher amplitudes of such current pulses might be necessary to obtain reliable measuring values.

In an embodiment, the computer-readable program causes the processor to automatically adapt an initial value of the width of current pulses used for measuring the impedance. In this context, the width of the current pulses can be chosen from a width range of from 5 µs to 200 µs, in particular from 10 µs to 150 µs, in particular from 20 µs to 120 µs, in particular from 30 µs to 90 µs. Current pulses having different widths are appropriate to a different extent to reliably measure the impedance.

In an embodiment, the computer-readable program causes the processor to automatically adapt an initial value of a measuring gain for measuring the impedance. In this context, the measuring gain values can be chosen from a gain range of from 1 to 600, in particular from 2 to 500, in particular from 3 to 400, in particular from 4 to 300, in particular from 5 to 150. By choosing an appropriate gain, comparatively low measuring values can be amplified to allow a reliable evaluation of the recorded signals.

In an embodiment, the computer-readable program causes the processor to measure the impedance in a unipolar manner between the first electrode pole of the electrode of the detection unit and the housing of the implantable medical device. Such a unipolar measuring of impedance is also typically applied when using a right ventricular electrode for an according impedance measurement. However, it should be noted that the measuring path is different in case of the His bundle electrode than in case of a right ventricular electrode since the housing of the implantable medical device is typically implanted at the same body site, wherein the His bundle electrode is located at a different cardiac site than a right ventricular electrode.

In another embodiment, the impedance is measured in a bipolar manner. In doing so, the computer-readable program causes the processor in this embodiment to measure the impedance between the first electrode pole and a second electrode pole of the electrode of the detection unit. Typically the first electrode pole is located at a distal tip of the His bundle electrode. In such a case, the second electrode pole is typically located proximally of the first electrode pole. The second electrode pole can be designed as a ring electrode pole. Measuring the cardiac impedance in a bipolar manner can be more appropriate in certain instances depending on the concrete site of implantation of the His bundle electrode.

In an embodiment, the computer-readable program causes the processor to use the measured impedance as input value for adjusting at least one physical parameter of a stimulation pulse to be delivered by the stimulation unit to the His bundle of the heart after having measured the impedance. Thus, the measured impedance can be used in an algorithm for adapting stimulation pulses to be subsequently applied to the heart, wherein the kind of stimulation like the stimulation strength or the stimulation rate can be adjusted in dependence on the determined contractility of the heart to be stimulated. In combination with the employed His bundle stimulation, a highly physiologic cardiac stimulation is thus possible.

In an aspect, the present invention relates to a method for controlling the operation of an implantable medical device according to the preceding explanations. This method comprises the steps explained in the following.

First, an electrical signal at the His bundle of the human or animal heart is measured with a detection unit of the implantable medical device. This measurement takes place upon termination of the first period of time, wherein the first period of time has started upon delivering of a stimulation pulse to the His bundle the same heart by a stimulation unit of the implantable medical device. In this context, the first period of time lies in time range of from 35 ms to 500 ms.

Upon delivering of the stimulation pulse, also a second period of time starts. When this second period of time is terminated (i.e., directly at the end of the second period of time), an impedance of the same heart is measured with the detection unit. The second period of time is equal to or longer than the first period of time. Additionally, it lies in a time range of from 50 ms to 500 ms.

In an aspect, the present invention relates to a computer program product comprising computer-readable code that causes the processor to perform the steps explained in the following when executed on the processor.

First, the His bundle of a human or animal heart is stimulated with a stimulation pulse delivered by a stimulation unit of an implantable medical device for stimulating a human or animal heart.

Upon delivering of the stimulation pulse, a first period of time starts. When the first period of time is terminated (i.e., directly at the end of the first period of time), an electric signal at the His bundle of the same heart is measured with a detection unit of the implantable medical device. In this context, the first period of time lies in time range of from 35 ms to 500 ms.

Upon delivering of the stimulation pulse, also a second period of time starts. When this second period of time is terminated (i.e., directly at the end of the second period of time), an impedance of the same heart is measured with the detection unit. The second period of time is equal to or longer than the first period of time. Additionally, it lies in a time range of from 50 ms to 500 ms.

In an aspect, the present invention relates to medical method for treating a human or animal patient in need of such treatment. This treatment is done with the help of an implantable medical device for stimulating a human or animal heart, in particular with the help of an implantable medical device according to the preceding explanations. As explained above, such an implantable medical device comprises a housing, a processor, a memory unit, a stimulation unit and a detection unit. The stimulation unit is configured to stimulate the His bundle of human or animal heart. The detection unit is configured to detect an electrical signal at the His bundle of the same heart. The method comprises the steps explained in the following.

First, the His bundle of a human or animal heart is stimulated with a first stimulation pulse delivered by the stimulation unit.

Upon delivering of the first stimulation pulse, a first period of time starts. When the first period of time is terminated (i.e., directly at the end of the first period of time), an electric signal at the His bundle of the same heart is measured with the detection unit. In this context, the first period of time lies in time range of from 35 ms to 500 ms.

Upon delivering of the first stimulation pulse, also a second period of time starts. When this second period of time is terminated (i.e., directly at the end of the second period of time), an impedance of the same heart is measured with the detection unit. The second period of time is equal to or longer than the first period of time. Additionally, it lies in a time range of from 50 ms to 500 ms.

The impedance is then used as input value for adjusting at least one physical parameter of a second stimulation pulse. Also the second stimulation pulse is to be delivered by the stimulation unit to the His bundle of the heart.

Finally, the second stimulation pulse is delivered to the His bundle of the heart by the stimulation unit so as to stimulate the His bundle of the heart once again.

All embodiments of the implantable medical device can be combined in any desired way and can be transferred either individually or in any arbitrary combination to the described methods and the described computer program product. Likewise, all embodiments of the described methods can be combined in any desired way and can be transferred either individually or in any arbitrary combination to the respective other method, to the implantable medical device and to the computer program product. Finally, all embodiments described with respect to the computer program product can be combined in any desired way and can be transferred either individually or in any arbitrary combination to the described implantable medical device or to the described methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be described in the following making reference to exemplary embodiments and accompanying Figures. In the Figures.

DETAILED DESCRIPTION

Figure 1:
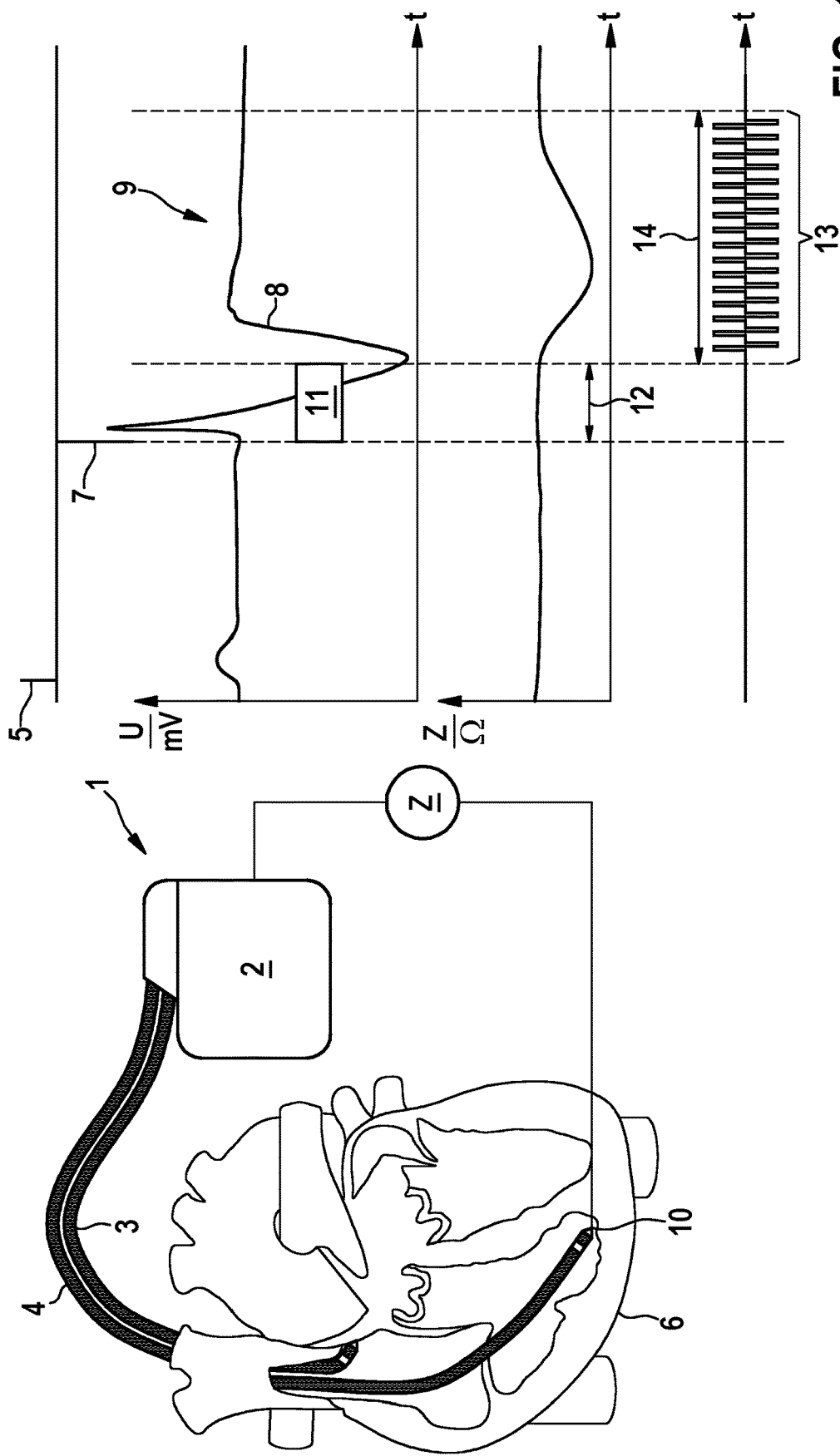
FIG. 1 shows a prior art setup for stimulating a human heart and measuring an impedance with a right ventricular electrode.

FIG. 1 shows a prior art setup for stimulating a human heart and measuring the impedance thereof. For this purpose, a pacemaker 1 is used. This pacemaker 1 comprises a housing 2 and is connected with a right atrial electrode 3 and a right ventricular electrode 4. The right atrial electrode 3 is used to detect a right atrial event 5. If this right atrial event 5 does not lead to a contraction of a human heart 6, a stimulation pulse 7 is delivered by the right ventricular electrode 4 to the right ventricle of the heart 6. This will lead to a capture response 8 in an intracardiac electrogram (IEGM) 9.

The right ventricular electrode 4 is also used to measure an impedance Z between an electrode pole 10 located at the distal tip of the right ventricular electrode 4 and the housing 2 of the pacemaker. This impedance Z will be detected after a blanking period 11. Thus, there is a delay 12 between the stimulation 7 by the right ventricular electrode 4 and the start of the impedance measurement. This delay 12 can also be denoted as $\Delta tmp_{RV-Z}$. The impedance measurement is carried out by a plurality of current pulses 13 that is applied during a standard impedance measuring time 14.

Figure 2:
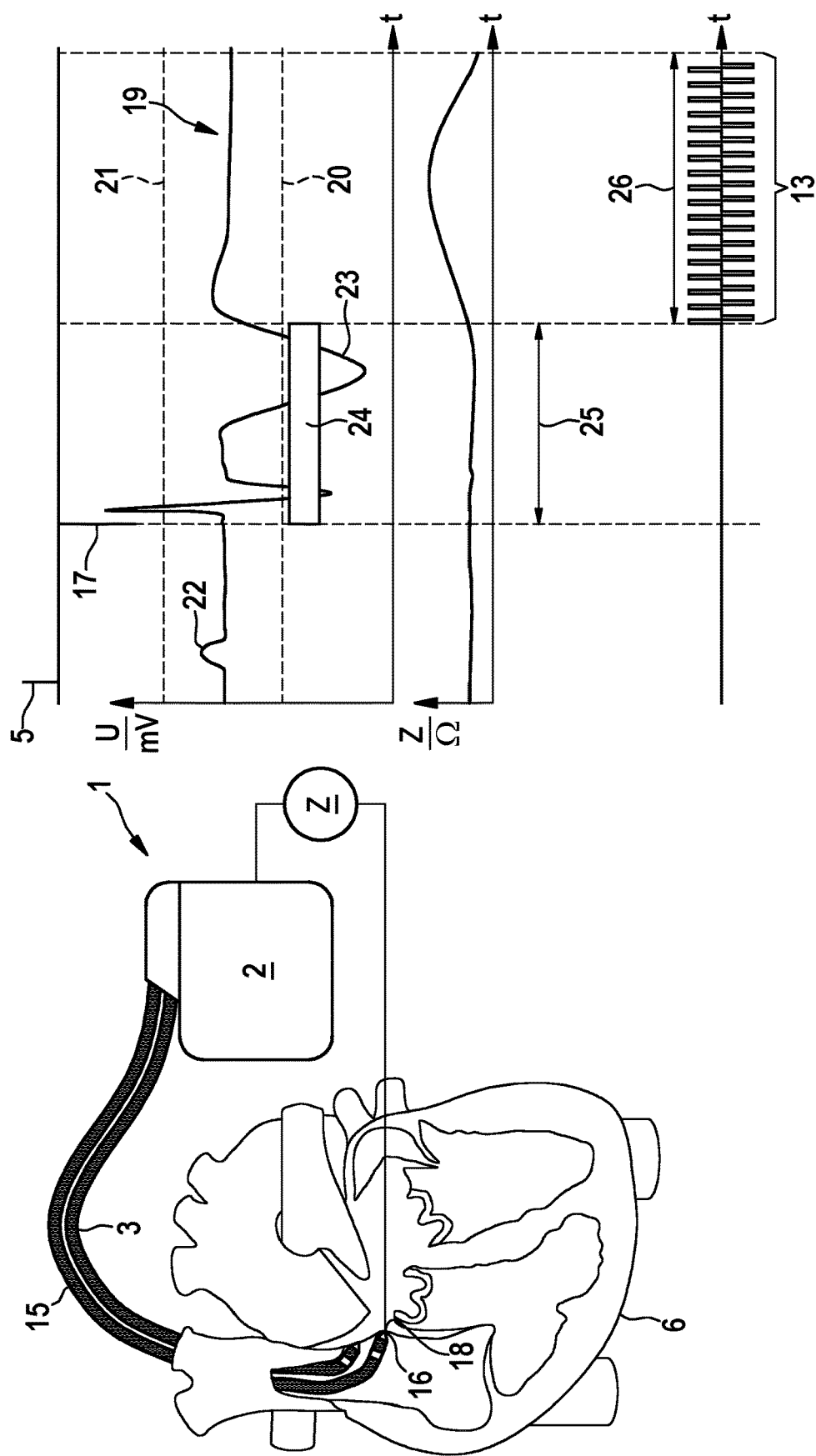
FIG. 2 shows a first embodiment of a setup for stimulating a human heart and measuring an impedance with a His bundle electrode.

FIG. 2 shows a first embodiment of a setup for stimulating a human heart with a His bundle electrode. In all Figures, similar elements will be denoted with the same numeral reference. The embodiment depicted in FIG. 2 employs an implantable pacemaker 1 serving as implantable medical device. This pacemaker 1 has a housing 2. Furthermore, a right atrial electrode 3 and His bundle electrode 15 are connected to the pacemaker 1. The His bundle electrode 15 comprises a His bundle electrode pole 16 at its distal end. This His bundle electrode pole 16 serves as first electrode pole. Upon detection of a right atrial signal 5 with the right atrial electrode 3, but no subsequent cardiac contraction, a stimulation pulse 17 will be delivered to the His bundle 18 with the His bundle electrode pole 16. This stimulation pulse 17 can be detected in an intracardiac electrogram (IEGM) 19 detected with the His bundle electrode 15.

A lower sensing threshold 20 and an upper sensing threshold 21 are previously determined such that neither a P wave 22 nor any His bundle activity will be sensed upon recording the IEGM 19. However, electrical signals evoked by an R wave 23 will be lower than the lower sensing threshold 20 or higher than the upper sensing threshold 21 so that they can be reliably detected (i.e., they have an intensity exceeding the lower sensing threshold 20 and/or the upper sensing threshold 21). However, the detection of the first R wave 23 following the stimulation pulse 17 will be suppressed by a first blanking window 24. This first blanking window 24 is equivalent to a first period of time 25 and extends from the stimulation pulse 17 until the end of the R wave 23 immediately following the stimulation pulse 17.

The first period of time 25 can also be denoted as $\Delta tmp_{HIS-Z}$. When comparing FIG. 2 with FIG. 1, it is apparent that the first period of time 25 is significantly longer than the delay 12 achieved by the blanking period 11 applied according to prior art techniques employing a right ventricular electrode.

The His bundle electrode 15 is also used for measuring an impedance Z between the His bundle electrode pole 16 and the housing 2 of the pacemaker 1. Measuring this impedance Z will only be started after the first period of time 25 has been terminated. The impedance Z is measured by a plurality of current pulses 13 applied by the His bundle electrode pole 16. An impedance measuring time 26 can be chosen to be significantly longer than the standard impedance measurement time 14 known from prior art. This longer impedance measuring time 26—serving as third period of time—accounts for less pronounced impedance variations detected with the His bundle electrode 15 than with the right ventricular electrode 4 (cf. FIG. 1).

Figure 3:
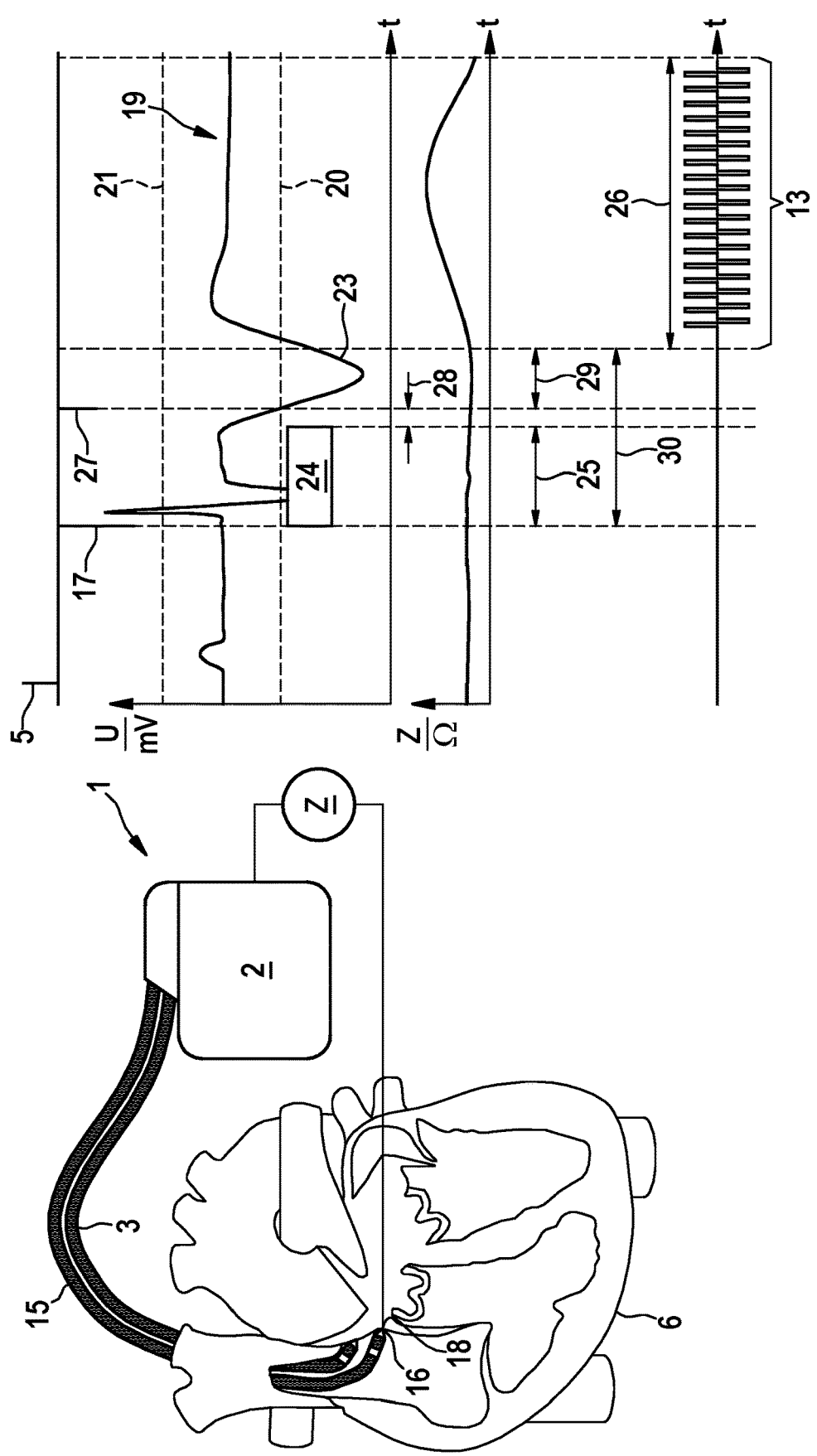
FIG. 3 shows a second embodiment of a setup for stimulating a human heart and measuring an impedance with a His bundle electrode.

FIG. 3 shows a second embodiment of a setup for stimulating a human heart and measuring an impedance with a His bundle electrode that equals in many aspects the embodiment shown in FIG. 2. Therefore, reference is made to the explanations of FIG. 2. In the following, only the differences between the embodiment of FIG. 2 and the embodiment of FIG. 3 will be explained.

The blanking window 24 and thus the first period of time 25 are in the embodiment of FIG. 3 significantly shorter than in the embodiment of FIG. 2. Consequently, after a first delay 28, an R wave 23 of a right ventricular event 27 can be detected once the depolarization of the ventricle of the stimulated human heart 6 is so intense that the voltage detected with the His bundle electrode 15 falls below the lower sensing threshold 20. Since the time of detection of the right ventricular event 27 is not fixed, the first delay 28 is variable and depends on the physiologic frame conditions and on the lower sensing threshold 20 and/or upper sensing threshold 21.

After having detected such a start of the right ventricular event 27, a second delay 29 is applied prior to starting measuring of the impedance Z. This second delay 29 extends over the R wave 23 of the right ventricular event 27 that is detected in the IEGM 19. Thus, the start of the impedance measurement will take place after the second delay 29, which can also be denoted as $\Delta tms_{HIS-Z}$, has terminated.

Expressed in other words, the measurement of the impedance Z will start upon termination of a second time period 30 that starts upon delivering of the stimulation pulse 17 and that comprises the first period of time 25 is first sub-period, the first delay 28 is second sub-period and the second delay 29 as third sub-period. Consequently, the second period of time 30 is longer than the first period of time 25 can be calculated as $\Delta tmp_{HIS-Z}$+first delay 28+$\Delta tms_{HIS-Z}$.

The measurement of the impedance Z itself will take place in the same manner as explained with respect to FIG. 2. In this context, the impedance measuring time 26 will be approximately the same as in case of the embodiment of FIG. 2 and thus significantly longer than the standard impedance measurement time 14 known from prior art.

Summarizing, the blanking window 24 in the embodiment of FIG. 2 is chosen such that it safely covers the expected R wave 23 after the stimulation pulse 17, whereas the blanking window 24 in the embodiment of FIG. 3 is chosen such that it safely does not cover the R wave 23 evoked in response to the stimulation pulse 17. Consequently, it is not possible with the embodiment of FIG. 2 to positively detect the expected R wave 23. This reduces the effort to be made in sensing the IEGM 19. In contrast, in the embodiment of FIG. 3, the R wave 23 is safely detected so that positive knowledge on the occurrence of this R wave 23 is given. This enhances the knowledge of the cardiac cycle by a more complete IEGM 19 than in case of the embodiment of FIG. 2 but requires more resources.

To avoid a start of the impedance measurement already during the R wave 23, an additional delay in form of the second delay 29 is applied in the embodiment of FIG. 3 so that the impedance measurement will only start after the second period of time 30 covering the first period of time 25, the first delay 28 and the second delay 29 has elapsed.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. Implantable medical device for stimulating a human or animal heart, comprising: a housing, a processor, a memory unit, a stimulation unit configured to stimulate the His bundle of a human or animal heart, and a detection unit configured to detect an electrical signal at the His bundle of the same heart, wherein the detection unit comprises an electrode having a first electrode pole,
wherein
the memory unit comprises a computer-readable program that causes the processor to perform the following steps when executed on the processor:
a) stimulating the His bundle of a human or animal heart with a stimulation pulse delivered by the stimulation unit;
b) measuring an electric signal at the His bundle of the same heart with the detection unit upon termination of a first period of time starting upon delivering of the stimulation pulse, wherein the first period of time lies in a time range of from 35 ms to 500 ms; and
c) measuring an impedance of the same heart with the detection unit upon termination of a second period of time starting upon delivering of the stimulation pulse, wherein the second period of time is equal to or longer than the first period of time and lies in a time range of from 50 ms to 500 ms.

2. Implantable medical device according to claim 1, wherein the computer-readable program causes the processor to determine and set a sensing threshold prior to step b), wherein the sensing threshold is lower than a signal intensity of an R wave of a cardiac contraction but higher than a signal of a P wave of a cardiac contraction and higher than a His bundle signal.

3. Implantable medical device according to claim 1, wherein the computer-readable program causes the processor to perform step c) without having detected an R wave of a cardiac contraction between steps a) and c), wherein the cardiac contraction has been evoked by the stimulation pulse.

4. Implantable medical device according to claim 1, wherein the computer-readable program causes the processor to detect an R wave of a cardiac contraction prior to step c), wherein the cardiac contraction has been evoked by the stimulation pulse.

5. Implantable medical device according to claim 4, wherein the second period of time comprises a first sub-period corresponding to the first period of time, a second sub-period extending from an end of the first sub-period until a detection of a right ventricular event, and a third sub-period extending from an end of the second sub-period until an end of the second period of time, wherein the third sub-period lies in a time range of from 10 ms to 100 ms.

6. Implantable medical device according to claim 1, wherein the computer-readable program causes the processor to conduct a plurality of impedance measurements during a third period of time starting at the end of the second period of time, wherein the third period of time lies in a time range of from 50 ms to 400 ms.

7. Implantable medical device according to claim 1, wherein the computer-readable program causes the processor to choose an initial value of an amplitude of current pulses for measuring the impedance from an amplitude range of from 5 µA to 1000 µA.

8. Implantable medical device according to claim 1, wherein the computer-readable program causes the processor to choose an initial value of a width of current pulses for measuring the impedance from width range of from 5 µs to 200 µs.

9. Implantable medical device according to claim 1, wherein the computer-readable program causes the processor to choose an initial value of a measuring gain for measuring the impedance from a gain range of from 1 to 600.

10. Implantable medical device according to claim 1, wherein the computer-readable program causes the processor to measure the impedance in a unipolar manner between the first electrode pole of the electrode of the detection unit and the housing of the implantable medical device.

11. Implantable medical device according to claim 1, wherein the computer-readable program causes the processor to measure the impedance in a bipolar manner between the first electrode pole and a second electrode pole of the electrode of the detection unit.

12. Implantable medical device according to claim 1, wherein the computer-readable program causes the processor to use the measured impedance as input value for adjusting at least one physical parameter of a stimulation pulse to be delivered by the stimulation unit to the His bundle of the heart after step c).

13. Method for controlling the operation of an implantable medical device according to claim 1, the method comprising the following steps:
 a) measuring an electric signal at the His bundle of a human or animal heart with a detection unit of the implantable medical device upon termination of a first period of time starting upon delivering of a stimulation pulse to the His bundle by a stimulation unit of the implantable medical device, wherein the first period of time lies in a time range of from 35 ms to 500 ms; and
 b) measuring an impedance of the same heart with a detection unit of the implantable medical device upon termination of a second period of time starting upon delivering of the stimulation pulse, wherein the second period of time is equal to or longer than the first period of time and lies in a time range of from 50 ms to 500 ms.

14. Method of treatment of a human or animal patient in need of such treatment by means of an implantable medical device according to claim 1 for stimulating a human or animal heart, wherein the implantable medical device comprises a housing, a processor, a memory unit, a stimulation unit configured to stimulate the His bundle of a human or animal heart, and a detection unit configured to detect an electrical signal at the His bundle of the same heart, the method comprising the following steps:
 a) stimulating the His bundle of a human or animal heart with a first stimulation pulse delivered by the stimulation unit;
 b) measuring an electric signal at the His bundle of the same heart with the detection unit upon termination of a first period of time starting upon delivering of the first stimulation pulse, wherein the first period of time lies in a time range of from 35 ms to 500 ms;
 c) measuring an impedance of the same heart with the detection unit upon termination of a second period of time starting upon delivering of the stimulation pulse, wherein the second period of time is equal to or longer than the first period of time and lies in a time range of from 50 ms to 500 ms;
 d) using the impedance as input value for adjusting at least one physical parameter of a second stimulation pulse to be delivered by the stimulation unit to the His bundle of the heart; and
 e) delivering the second stimulation pulse to the His bundle of the heart by the stimulation unit.

15. Computer program product comprising computer-readable code that causes a processor to perform the following steps when executed on the processor:
 a) stimulating the His bundle of a human or animal heart with a stimulation pulse delivered by a stimulation unit of an implantable medical device for stimulating a human or animal heart;
 b) measuring an electric signal at the His bundle of the same heart with a detection unit of the implantable medical device upon termination of a first period of time starting upon delivering of the stimulation pulse, wherein the first period of time lies in a time range of from 35 ms to 500 ms; and
 c) measuring an impedance of the same heart with the detection unit upon termination of a second period of time starting upon delivering of the stimulation pulse, wherein the second period of time is equal to or longer than the first period of time and lies in a time range of from 50 ms to 500 ms.

\* \* \* \* \*